United States Patent
Rothermel et al.

(10) Patent No.: US 7,030,147 B2
(45) Date of Patent: Apr. 18, 2006

(54) COMBINATIONS COMPRISING AN ANTIDIARRHEAL AGENT AND AN EPOTHILONE OR AN EPOTHILONE DERIVATIVE

(75) Inventors: John David Rothermel, Randolph, NJ (US); Horst F. Schran, Morristown, NJ (US); Diane Greeley, Watchung, NJ (US); TianLing Chen, Florham Park, NJ (US)

(73) Assignee: Novartis AG, Basel (CH)

( * ) Notice: Subject to any disclaimer, the term of this patent is extended or adjusted under 35 U.S.C. 154(b) by 252 days.

(21) Appl. No.: 10/471,904

(22) PCT Filed: Mar. 18, 2002

(86) PCT No.: PCT/EP02/02977

§ 371 (c)(1),
(2), (4) Date: Sep. 15, 2003

(87) PCT Pub. No.: WO02/074042

PCT Pub. Date: Sep. 26, 2002

(65) Prior Publication Data

US 2004/0092478 A1    May 13, 2004

Related U.S. Application Data

(60) Provisional application No. 60/277,153, filed on Mar. 19, 2001, provisional application No. 60/277,207, filed on Mar. 20, 2001.

(51) Int. Cl.
*A61K 43/78* (2006.01)
*A61K 31/425* (2006.01)
*A61K 43/00* (2006.01)
*A61K 31/33* (2006.01)
*A61K 43/02* (2006.01)

(52) U.S. Cl. ............. 514/365; 514/9; 514/10; 514/11; 514/163; 514/183; 514/186; 514/210.17; 514/282; 514/315; 514/327; 514/329; 514/330; 514/371; 514/372; 514/423; 514/449; 514/450; 514/867; 514/974; 424/653; 424/725; 424/776

(58) Field of Classification Search .............. 514/9, 514/10, 11, 163, 183, 186, 210.17, 282, 315, 514/327, 329, 330, 365, 371, 372, 423, 449, 514/450, 867, 974; 424/653, 725, 776
See application file for complete search history.

(56) References Cited

U.S. PATENT DOCUMENTS

| | | | | |
|---|---|---|---|---|
| 5,969,145 A | * | 10/1999 | Schinzer et al. | 548/110 |
| 5,977,163 A | * | 11/1999 | Li et al. | 514/449 |
| 6,040,321 A | * | 3/2000 | Kim et al. | 514/369 |
| 6,103,487 A | * | 8/2000 | Barnett et al. | 435/15 |
| 6,127,390 A | * | 10/2000 | deSolms et al. | 514/341 |
| 6,302,838 B1 | * | 10/2001 | O'Reilly et al. | 514/365 |

FOREIGN PATENT DOCUMENTS

WO    WO 01 92255    12/2001

OTHER PUBLICATIONS

Altaha, Ramin et al., "Epothilones: A novel class of non-taxane microtubule-stabilizing agents," Current Pharmaceutical Design, vol. 8(19), pp. 1707-1712 (2002).

* cited by examiner

*Primary Examiner*—John Pak
*Assistant Examiner*—David P. Stitzel
(74) *Attorney, Agent, or Firm*—Oona A. Jackson; Lydia T. McNally

(57) ABSTRACT

Epothilone derivatives are co-administered with an antidiarrheal agent, e.g., a DPP-IV inhibitor, in the treatment of a proliferative disease.

9 Claims, No Drawings

COMBINATIONS COMPRISING AN ANTIDIARRHEAL AGENT AND AN EPOTHILONE OR AN EPOTHILONE DERIVATIVE

This application is a 371 of PCT application PCT/EP02/02977, which was filed on Mar. 18, 2002, and claims benefit of U.S. Provisional Application No. 60/277,153, filed Mar. 19, 2001 and U.S. Provisional Application No. 60/277,207, filed Mar. 20, 2001.

The invention relates to a pharmaceutical combination which comprises (a) an antidiarrheal agent, in particular, a dipeptidylpeptidase-IV (DPP-IV) inhibitor, (b) an epothilone derivative of formula I, and optionally at least one pharmaceutically acceptable carrier for simultaneous, separate or sequential use, in particular for the treatment of a proliferative disease, especially a solid tumor disease; a pharmaceutical composition comprising such a combination; the use of such a combination for the preparation of a medicament for the treatment of a proliferative disease; a commercial package or product comprising such a combination as a combined preparation for simultaneous, separate or sequential use; and to a method of treatment of a warm-blooded animal, especially a human.

The microtubule-stabilizing effect of epothilones was first described by Boliag et al., Cancer Research 55, 1995, 2325–33. A suitable treatment schedule of different types of tumors, especially tumors which are refractory to the treatment by other chemotherapeutics, in particular TAXOL™, is described in WO 99/43320.

The present invention pertains to a combination, such as a combined preparation or a pharmaceutical composition, which comprises (a) an antidiarrheal agent and (b) an epothilone derivative of formula I

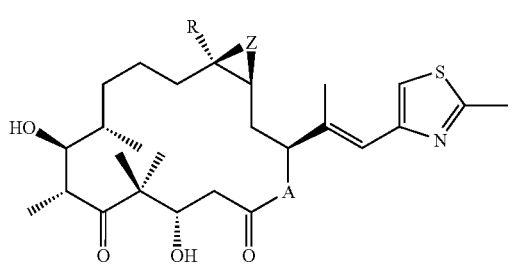

(I)

in which compound A represents O or NR$_N$, wherein R$_N$ is hydrogen or lower alkyl, R is hydrogen or lower alkyl, and Z is O or a bond, in which the active ingredients (a) and (b) are present in each case in free form or in the form of a pharmaceutically acceptable salt and optionally at least one pharmaceutically acceptable carrier; for simultaneous, separate or sequential use.

A compound of formula I wherein A represents O, R is hydrogen and Z is O is known as epothilone A; a compound of formula I wherein A represents O, R is methyl and Z is O is known as epothilone B; a compound of formula I wherein A represents O, R is hydrogen and Z is a bond is known as epothilone C; a compound of formula I wherein A represents O, R is methyl and Z is a bond is known as epothilone D.

The term "a combined preparation", as used herein defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g. in order to cope with the needs of a patient sub-population to be treated or the needs of the single patient based on the severity of the diarrhea that the patient experiences.

The present invention especially relates to a combined preparation, which comprises (a) one or more unit dosage forms of an antidiarrheal agent and (b) one or more unit dosage forms of an epothilone derivative of formula I, especially epothilone B.

The antidiarrheal agent is administered to prevent, control or eliminate diarrhea that is sometimes associated with the administration of epothilones, especially epothilone B. Thus, the present invention also relates to a method of preventing or controlling diarrhea associated with administering an epothilone derivative of formula I, which comprises administering an effective amount of an antidiarrheal agent to the patient receiving treatment with the epothilone derivative.

The term "solid tumor" especially means breast cancer, ovarian cancer, cancer of the colon and generally the GI tract, cervix cancer, lung cancer, in particular small-cell lung cancer, and non-small-cell lung cancer, head and neck cancer, bladder cancer, cancer of the prostate or Kaposi's sarcoma. The present combination inhibits the growth of solid tumors, but also liquid tumors. Furthermore, depending on the tumor type and the particular combination used a decrease of the tumor volume can be obtained. The combinations disclosed herein are also suitable to prevent the metastatic spread of tumors and the growth or development of micrometastases.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

It will be understood that references to the combination partners (a) and (b) are meant to also include the pharmaceutically acceptable salts. If these combination partners (a) and (b) have, for example, at least one basic center, they can form acid addition salts. Corresponding acid addition salts can also be formed having, if desired, an additionally present basic center. The combination partners (a) and (b) having an acid group (for example COOH) can also form salts with bases. The combination partner (a) or (b) or a pharmaceutically acceptable salt thereof may also be used in form of a hydrate or include other solvents used for crystallization.

Epothilone derivatives of formula I wherein A represents O or NR$_N$, wherein R$_N$ is hydrogen or lower alkyl, R is hydrogen or lower alkyl and Z is O or a bond, and methods for the preparation of such epothilone derivatives are in particular generically and specifically disclosed in the patents and patent applications WO 93/10121, U.S. Pat. No. 6,194,181, WO 98/25929, WO 98/08849, WO 99/43653, WO 98/22461 and WO 00/31247 in each case in particular in the compound claims and the final products of the working examples, the subject-matter of the final products, the pharmaceutical preparations and the claims is hereby incorporated into the present application by reference to this publications. Comprised are likewise the corresponding stereoisomers as well as the corresponding crystal modifications, e.g. solvates and polymorphs, which are disclosed therein.

The transformation of epothilone B to the corresponding lactam is disclosed in Scheme 21 (page 31, 32) and Example 3 of WO 99/02514 (pages 48–50). The transformation of a compound of formula I which is different from epothilone B into the corresponding lactam can be accomplished analogously. Corresponding epothilone derivatives of formula I wherein $R_N$ is lower alkyl can be prepared by methods known in the art such as a reductive alkylation reaction starting from the epothilone derivative wherein $R_N$ is hydrogen.

Epothilone derivatives of formula 1, especially epothilone B, can be administered as part of pharmaceutical compositions which are disclosed in WO 99/39694.

In a specific embodiment, the epothilone derivative is a compound of formula I in which compound A represents O or $NR_N$, wherein $R_N$ is hydrogen or lower alkyl, R is hydrogen or lower alkyl, and Z is O or a bond.

In the epothilone derivative of formula I preferably A represents O, R is lower alkyl, e.g. ethyl or, most preferably, methyl and Z is preferably O.

Antidiarrheal agents and protocols for their administration are known to those skilled in the art. Antidiarrheal agents suitable for use in the inventive methods and compositions include, but are not limited to, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents. In one embodiment of the invention, the antidiarrheal agent is selected from codeine, tincture of opium, paregoric, diphenoxylate, difenoxine and loperamide. In another embodiment of the invention, the antidiarrheal agent is selected from lanreotide, vapreotide and octreotide. Of these three compounds, octreotide is especially preferred. The latter compound or its acetate can be obtained and employed as described in U.S. Pat. No. 4,395,403, or, e.g., in the form of its acetate or pamoate as described in U.S. Pat. No. 5,538,739. In particular, octreotide can be administered to the patient as marketed under the trademarks SANDOSTATIN™ and SANDOSTATIN LAR™.

The antidiarrheal agent employed in the present invention can also be a DPP-IV inhibitor. DPP-IV inhibitors are known in the art for the treatment of diabetes. Protocols for their administration in the treatment of diabetes are known to those skilled in the art. However, in the present invention the DPP-IV inhibitor functions to prevent and/or control diarrhea that is sometimes associated with the administration of epothilone derivatives.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or non-peptidic. Preferably, the DPP-IV inhibitor is non-peptidic.

Preferably, DPP-IV inhibitors are employed in the present invention which are generically and specifically disclosed in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. DPP728 and LAF237 are specifically disclosed in Example 3 of WO 98/19998 and Example 1 of WO 00/34241, respectively. A further suitable DPP-IV inhibitor of formula VI (see below) is specifically described in Diabetes 1998, 47, 1253–1258. DPP728 can be formulated as described on page 20 of WO 98/19998.

N-Peptidyl-O-aroyl hydroxylamines, e.g. of formula VII or VIIa (see below), and their preparation are described by H. U. Demuth et al. in J. Enzyme Inhibition 1988, Vol. 2, pages 129–142, especially on pages 130–132.

Unless stated otherwise in the present disclosure organic radicals designated "lower" contain not more than 7, preferably not more than 4, carbon atoms and the following expressions have the meanings as given below:

Halogen represents preferably fluoro, chloro or bromo.

Lower alkyl is, if not stated otherwise, preferably ethyl or, most preferably, methyl. $(C_{1-8})$Alkyl is branched or preferably unbranched alkyl, preferably lower alkyl, e.g. methyl or ethyl.

Lower alkylene is preferably methylene, ethylene or propylene. It can be unsubstituted or substituted e.g. by hydroxy.

Lower alkoxy is preferably methoxy or ethoxy. $(C_{2-4})$Alkoxy is e.g. ethoxy or propoxy.

Cycloalkyl is e.g. $C_3$–$C_{12}$cycloalkyl, preferably cyclopropyl, cyclobutyl, cyclopentyl, cyclohexyl, cycloheptyl or cyclodecyl; or bicycloalkyl such as bicycloheptyl. Cycloalkenyl is preferably 1-cyclohexenyl, 2-cyclohexenyl, 3-cyclohexenyl, 1-cyclopentenyl or 1-cyclopentenyl.

$(C_{1-3})$Hydroxyalkyl is e.g. 3-hydroxypropyl, 1-hydroxyethyl or hydroxymethyl.

$C_4$–$C_6$-Alkylenimino which is unsubstituted or substituted by one or two lower alkyl groups is, for example, pyrrolidinyl, methylpyrrolidinyl, 1-piperidinyl, 2-piperidinyl, 3-piperidinyl, 2methyl -1-piperidinyl or hexamethylenimino. Preferably, $C_4$–$C_6$-alkylenimino is 1-piperidinyl.

A [3.1.1]bicyclic carbocyclic moiety optionally substituted as defined above preferably is bicyclo[3.1.1]hept-2-yl optionally disubstituted in 6-position with methyl, or bicyclo [3.1.1]hept-3-yl optionally trisubstituted with one methyl in 2-position and two methyl groups in 6-position. A [2.2.1] bicyclic carbocyclic moiety optionally substituted as defined above preferably is bicyclo[2.2.1]hept-2-yl.

Aryl comprises preferably 6 to 12 carbon atoms and is e.g. phenyl, tolyl or naphthyl, each of which can be substituted e.g. by lower alkyl or halogen.

The term "heteroaryl" refers to an aromatic heterocyclic radical selected, for example, from the group consisting of pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, azepinyl, 4-piperidinyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane, indolyl, benzothiazolyl, benzoxazolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl, dihydrobenzoisothiazolyl, dihydroisoindolyl, dihydroquinazolinyl and tetrahydroquinazolinyl.

Preferred DPP-IV inhibitors are N—(N'-substituted glycyl)-2-cyanopyrrolidines represented by formula (I),

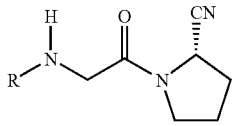  (I)

wherein R is:
a) $R_1R_{1a}N(CH_2)_m$— wherein
   $R_1$ is a pyridinyl or pyrimidinyl moiety optionally mono- or independently disubstituted with lower alkyl, lower alkoxy, halogen, trifluoromethyl, cyano or nitro; or phenyl optionally mono- or independently disubstituted with lower alkyl, lower alkoxy or halogen;
   $R_{1a}$ is hydrogen or $(C_{1-8})$alkyl; and
   m is 2 or 3;
b) $(C_{3-12})$cycloalkyl optionally monosubstituted in the 1-position with $(C_{1-3})$hydroxyalkyl;
c) $R_2(CH_2)_n$— wherein either
   $R_2$ is phenyl optionally mono- or independently di- or independently trisubstituted with lower alkyl, lower alkoxy, halogen or phenylthio optionally monosubstituted in the phenyl ring with hydroxymethyl; or is $(C_{1-8})$alkyl; a [3.1.1]bicyclic carbocyclic moiety optionally mono- or plurisubstituted with $(C_{1-8})$alkyl; a pyridinyl or naphthyl moiety optionally mono- or independently disubstituted with lower alkyl, lower alkoxy or halogen; cyclohexene; or adamantyl; and
   n is 1 to 3; or
   $R_2$ is phenoxy optionally mono- or independently disubstituted with lower alkyl, lower alkoxy or halogen; and
   n is 2 or 3;
d) $(R_3)_2CH(CH_2)_2$— wherein each $R_3$ independently is phenyl optionally mono- or independently disubstituted with lower alkyl, lower alkoxy or halogen;
e) $R_4(CH_2)_p$— wherein $R_4$ is 2-oxopyrrolidinyl or $(C_{2-4})$alkoxy and p is 2 to 4;
f) Isopropyl optionally monosubstituted in 1-position with $(C_{1-3})$hydroxyalkyl;
g) $R_5$ wherein $R_5$ is: indanyl; a pyrrolidinyl or piperidinyl moiety optionally substituted with benzyl; a [2.2.1]- or [3.1.1]bicyclic carbocyclic moiety optionally mono- or plurisubstituted with $(C_{1-8})$alkyl; adamantyl; or $(C_{1-8})$alkyl optionally mono- or independently plurisubstituted with hydroxy, hydroxymethyl or phenyl optionally mono- or independently disubstituted with lower alkyl, lower alkoxy or halogen;
h) a substituted adamantyl in free form or in acid addition salt form.

In a preferred embodiment of the invention, the N—(N'-substituted glycyl)-2-cyano-pyrrolidine is represented by formula (I), wherein
R is $R_1R_{1a}N(CH_2)_m$— wherein
   $R_1$ is a pyridinyl or pyrimidinyl moiety optionally mono- or independently disubstituted with lower alkyl, lower alkoxy, halogen, trifluoromethyl, cyano or nitro; or phenyl optionally mono- or independently disubstituted with lower alkyl, lower alkoxy or halogen;
   $R_{1a}$ is hydrogen or $(C_{1-8})$alkyl; and
   m is 2 or 3;

in free form or in acid addition salt form.

More preferably, the N—(N'-substituted glycyl)-2-cyanopyrrolidine is represented by formula (I), wherein
R is $R_1R_{1a}N(CH_2)_m$— wherein
   $R_1$ is a pyridinyl moiety optionally mono- or iridependently disubstituted with lower alkyl, lower alkoxy, halogen, trifluoromethyl, cyano or nitro;
   $R_{1a}$ is hydrogen or $(C_{1-8})$alkyl; and
   m is 2 or 3;

in free form or in acid addition salt form.

Most preferably, the N—(N'-substituted glycyl)-2-cyanopyrrolidine of formula I is (S)-1-{2-[5-cyanopyridin-2-yl)amino]ethyl-aminoacetyl}-2-cyano-pyrrolidine (DPP728) or (S)-1-[(3-hydroxy-1-adamantyl)amino]acetyl-2-cyano-pyrrolidine (LAF237).

In another preferred embodiment, the DPP-IV inhibitor is selected from the compounds of formulae II, III, IV and V:

A-B  (formula II, groups G1 and G2)

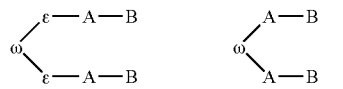

(formula III, group G3)   (formula IV, group G3)   and

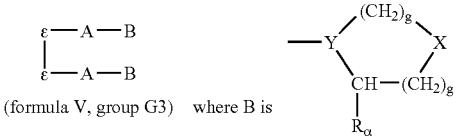

(formula V, group G3)   where B is f is 1 or 2;
g is 0, 1 or 2;
X is $CH_2$, O, S, SO, $SO_2$, NH or $NR\alpha_1$ where $R\alpha_1$ is lower alkyl ($C_1$ to $C_6$);
—Y is —N, —CH or —C= (when the —CO group of A is replaced with —CH= or —CF=);
$R\alpha$ is H, CN, CHO, $B(OH)_2$, $PO_3H$ or an ester thereof, CC—$R\alpha_7$, or CH=N—$R\alpha_8$ where $R\alpha_7$ is H, F, lower alkyl ($C_1$ to $C_6$), CN, $NO_2$, $OR\alpha_9$, $CO_2R\alpha_9$ or $COR\alpha_9$; $R\alpha_9$ is lower alkyl ($C_1$ to $C_6$); $R\alpha_8$ is Ph, OH, $OR\alpha_9$, $OCOR\alpha_9$ or OBn; A is attached to Y;

and wherein for the group G1 compounds
(a) when $R\alpha$ is H, A is an α-amino-acyl group derived from an α-amino-acid bearing a cycloaliphatic side-chain or is a β-amino-acyl group of general formula

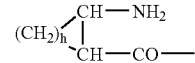

where h is 1 to 6, the ring in either case optionally having unsaturation and/or heteroatom substitution;
(b) when $R\alpha$ is CN, CC—$R\alpha_7$, or CH=N—$R\alpha_8$, A is as defined at (a) and in addition may be derived from any L-α-amino acid bearing a lipophilic side-chain;
(c) and when $R\alpha$ is CHO or $B(OH)_2$, A is a β-amino-acyl group as defined under (a);

for the group G2 compounds, $R\alpha$ is H, CN, C=C—$R\alpha_7$ or —CH=N—$R\alpha_8$ and A is

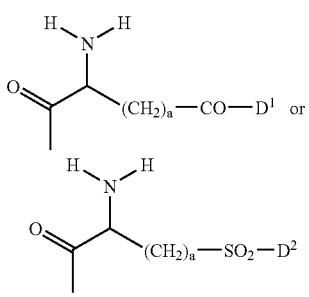

where a is 1–5; $D^1$ is -G-$(CH_2)_b$—$(R\alpha_4)_q$—$R\alpha_3$; G is O, NH or NMe; b is 0–5; $D^2$ is $D^1$ with G≠O; $R\alpha_4$ is Z-NH—$(CH_2)_c$— or NH-Z-$(CH_2)_c$— where c is 1–12 and Z is CO, $CH_2$ or $SO_2$; $R\alpha_3$ is $CO_2H$ or an ester thereof, $CONH_2$, $CONHNH_2$, $CONR\alpha_5R\alpha_5$, $CONHNR\alpha_5R\alpha_6$, $PO_3H$ or an ester thereof, $SO_3H$, $SO_2NH_2$, $SO_2NR\alpha_5R\alpha_6$, OH, $OR\alpha_5$, substituted or unsubstituted aryl or heteroaryl, $NH_2$, $NR\alpha_5R\alpha_6$, $NHCO_2R\alpha_5$, $NHSO_2NR\alpha_5R\alpha_6$, $NHCOR\alpha_5$, NH—$SO_2R\alpha_5$, NH—$CH(:NR\alpha_5)NR\alpha_5R\alpha_6$, $NHCONHR\alpha_5R\alpha_6$, sugar, CO-aminosugar, NHCO-aminosugar or NHCS-aminosugar; and $R\alpha_5$ and $R\alpha_6$ are independently selected from H and lower alkyl, fluoroalkyl and cycloalkyl group of up to 8 atoms and aryl, heteroaryl and alkyl heteroaryl groups of up to 11 atoms or $R\alpha_5$ and $R\alpha_6$ may together comprise a chain ($C_3$ to $C_8$); or is

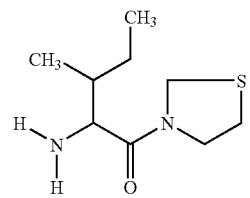

where $R\alpha_{10}$ is H or Me, the ring may contain more heteroatoms, E is J-$(CH_2)_b$—$(R\alpha_4)_q$—$R\alpha_3$, J=CO, $CH_2$ or $SO_2$, and a, b, q, $R\alpha_3$ and $R\alpha_4$ are as defined under (i); or is

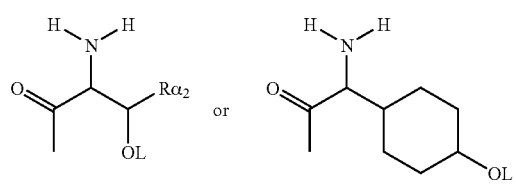

where $R\alpha_2$ is H or Me, the ring may contain one or more heteroatoms, and L is $(CH_2)_d$—$(CO)_r$—$(CH_2)_b$—$(R\alpha_4)_q$—$R\alpha_3$ or $(CH_2)_e$—$NR\alpha_{10}(CH_2)_b$—$(R\alpha_4)_q$—$R\alpha_3$ where r is 0 or 1, d is 0–4, e is 2–4, and b, q, $R\alpha_3$ and $R\alpha_4$ are as defined under (i);

and for the group G3 compounds, each B may have any identity defined therefor above, each A may be chosen from any group G2 structure (i), (ii) or (iii) above with the terminal groups $R\alpha_3$ in the A residues replaced with a shared group -ε-ω-ε- or -ε-ε- or -ω-, and ε and ω are selected independently from $CH_2$, O, NH, CO, S, $SO_2$, Ph and NHMe;

and wherein in groups G2 and G3 at least one $CH_2$ group in a chain may be replaced by a bioisostere thereof or any amide group which connects A and B in a group G1, G2 or G3 compound or which is in a side-chain of A in a Group G2 or G3 compound may be replaced by an amide bioisostere, in free form or in acid addition salt form.

In another preferred embodiment, the DPP-IV inhibitor is a compound of formula VI

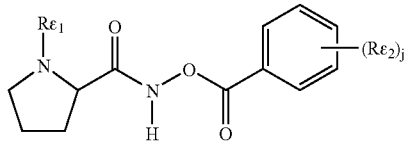

in free form or in acid addition salt form.

In a further preferred embodiment, the DPP-IV inhibitor is a N-peptidyl-O-aroyl hydroxylamine or a pharmaceutically acceptable salt thereof. Aroyl is, for example, naphthylcarbonyl; or benzoyl which is unsubstituted or mono- or disubstituted, for example, by lower alkoxy, lower alkyl, halogen or, preferably, nitro. The peptidyl moiety comprises preferably two α-amino acids, e.g. glycine, alanine, leucine, phenylalanine, lysine or proline, of which the one attached directly to the hydroxylamine nitrogen atom is preferably proline.

Preferably, the N-peptidyl-O-aroyl hydroxylamine is a compound of formula VII (VII)

wherein j is 0, 1 or 2;

$R\epsilon_1$ represents the side chain of a natural amino acid; and $R\epsilon_2$ represents lower alkoxy, lower alkyl, halogen or nitro;

or a pharmaceutically acceptable salt thereof.

In a very preferred embodiment of the invention, the N-peptidyl-O-aroyl hydroxylamine is a compound of formula VIIa

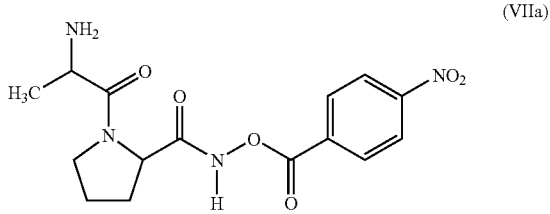

(VIIa)

or a pharmaceutically acceptable salt thereof.

In a highly preferred embodiment, the component (a) DPP-IV inhibitor is (S)-1-{2-[5-cyano-pyridin-2-yl)amino] ethyl-aminoacetyl}-2-cyano-pyrrolidine (DPP728), and the component (b) epothilone derivative is epothilone B.

In another highly preferred embodiment, the component (a) DPP-IV inhibitor is (S)-1-[(3-hydroxy-1-adamantyl) amino]acetyl-2-cyano-pyrrolidine (LAF237) and the component (b) epothilone derivative is epothilone B.

The present invention especially relates to a combined preparation, which comprises (a) one or more unit dosage forms of an DPP-IV inhibitor and (b) one or more unit dosage forms of an epothilone derivative of formula I, especially epithilone B.

A combination which comprises (a) an antidiarrheal agent and (b) an epothilone derivative of formula I in which compound A represents O or $NR_N$, wherein $R_N$ is hydrogen or lower alkyl, R is hydrogen or lower alkyl, and Z is O or a bond, in which the active ingredients are present in each case in free form or in the form of a pharmaceutically acceptable salt and optionally at least one pharmaceutically acceptable carrier, will be referred to hereinafter as a COMBINATION OF THE INVENTION.

When the combination partners employed in the COMBINATION OF THE INVENTION are applied in the form as marketed as single drugs, their dosage and mode of administration can take place in accordance with the information provided on the package insert of the respective marketed drug in order to result in the beneficial effect described herein, if not mentioned herein otherwise.

The antidiarrheal agent is administered as a preventative measure throughout the cycle or as needed when diarrhea occurs.

In a preferred embodiment of the present invention, the subject receives the epothilone derivative of formula I once weekly for several weeks, for example three weeks, followed by one or several weeks off and the antidiarrheal agent is administered as a preventative measure by pretreating the subject with the antidiarrheal agent before the administration of the epothilone derivative begins and continuing administration of the antidiarrheal agent throughout the cycles, or by administering the antidiarrheal agent throughout the cycles without pretreatment or by administering antidiarrheal agent as needed when diarrhea occurs during the cycles, with or without a pretreatment. As an example, when the epothilone derivative is administered once weekly for three weeks with one week off, each four week interval will be considered one cycle.

An effective amount of the antidiarrheal agent is an amount sufficient to prevent, control, or eliminate diarrhea associated with the administration of an epothilone derivative, especially it is an amount which increases the amount of the epothilone derivative that can administered when the diarrhea is the does limiting toxicity of the epothilone derivative, especially epothilone B.

The COMBINATION OF THE INVENTION can be a combined preparation or a pharmaceutical composition.

It is one objective of this invention to provide a pharmaceutical composition comprising a quantity, which is therapeutically effective against a proliferative disease comprising the COMBINATION OF THE INVENTION, i.e., in such pharmaceutical composition the combination partners (a) and (b) are administered together in a fixed combination.

The pharmaceutical compositions according to the invention can be prepared in a manner known per se and are those suitable for enteral, such as oral or rectal, and parenteral administration to mammals (warm-blooded animals), including man.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils, alcohols, flavoring agents, preservatives, coloring agents; or carriers such as starches, sugars, microcristalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed.

In particular, a therapeutically effective amount of each of the combination partner of the COMBINATION OF THE INVENTION may be administered separately, i.e., the components may be administered simultaneously or sequentially and in any order. For example, the method of treatment of a proliferative disease according to the invention may comprise (i) administration of the first combination partner in free or pharmaceutically acceptable salt form and (ii) administration of the second combination partner in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners of the COMBINATION OF THE INVENTION can be administered separately at different times during the course of therapy or concurrently in divided or single combination forms. One agents can, e.g., be an enteral formulation and the other can be administered parenterally. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the epothilone derivative within the range that yields efficacy without toxicity requires a regimen based on the kinetics of the active ingredients' availability to target sites. This involves a consideration of the distribution, equilibrium, and elimination of the active ingredients.

If the the warm-blooded animal is a human, the dosage of a compound of formula I is preferably in the range of about 0.25 to 75, preferably 0.5 to 50, e.g. 2.5, mg/m² once weekly for two to four, e.g. three, weeks, followed by 6 to 8 days off in the case of an adult patient.

The antidiarrheal agent is preferably administered from one to four times per day according to established protocols for the antidiarrheal agent.

A DPP-IV inhibitor, if employed, is preferably administered according to known protocols for the treatment of diabetes. Preferably, the dose is in the range from 25 mg to 1000 mg per day.

Moreover, the present invention relates to a method of treating a warm-blooded animal having a proliferative disease comprising administering to the animal a COMBINATION OF THE INVENTION in a quantity which is therapeutically effective against a proliferative disease and which reduces any diarrhea associated with the administration of the epothilone derivative.

Furthermore, the present invention pertains to the use of a COMBINATION OF THE INVENTION for the treatment of a proliferative disease and for the preparation of a medicament for the treatment of a proliferative disease.

Moreover, the present invention provides a commercial package comprising as active ingredients COMBINATION OF THE INVENTION, together with instructions for simultaneous, separate or sequential use thereof in the treatment of a proliferative disease.

The following Examples illustrate the invention described above; they are not, however, intended to limit the scope of the invention in any way. The beneficial effects of the COMBINATION OF THE INVENTION can also be determined by other test models known as such to the person skilled in the pertinent art.

EXAMPLE 1

A human patient suffering from a proliferative disease is treated with 6 cycles of epothilone B wherein each cycle consists of a once a week administration of 2.5 mg epothilone B as a 5 minute bolus or as a 15 minute bolus for three weeks followed by 14 days of rest. Throughout the treatment the patient receives from 2 mg to 16 mg of loperamide daily as its hydrochloride salt to control diarrhea.

EXAMPLE 2

A human patient suffering from a proliferative disease is treated with 6 cycles of epothilone B wherein each cycle consists of 2.5 mg epothilone B administered as a 5 minute bolus once a week for three weeks followed by 14 days of rest. The patient receives up to 16 mg of loperamide as its hydrochloride salt to daily when diarrhea occurs.

EXAMPLE 3

A human patient suffering from a proliferative disease is treated with 6 cycles of epothilone B wherein each cycle consists of 2.5 mg epothilone B administered as a 5 minute bolus once a week for three weeks followed by 14 days of rest. Throughout the treatment the patient receives from one to six 50 mg doses of DPP728 daily to control diarrhea.

EXAMPLE 4

A human patient suffering from a proliferative disease is treated with 6 cycles of epothilone B wherein each cycle consists of 2.5 mg epothilone B administered as a 5 minute bolus once a week for three weeks followed by 14 days of rest. The patient receives up to 300 mg of DPP728 daily when diarrhea occurs.

EXAMPLE 5

A human patient suffering from a proliferative disease is treated with 6 cycles of epothilone B wherein each cycle consists of 2.5 mg epothilone B administered as a 15 minute bolus once a week for three weeks followed by 14 days of rest. Throughout the treatment the patient receives from one to six 50 mg doses of LAF 237 daily to control diarrhea.

EXAMPLE 6

A human patient suffering from a proliferative disease is treated with 6 cycles of epothilone B wherein each cycle consists of 2.5 mg epothilone B administered as a 5 minute bolus once a week for three weeks followed by 14 days of rest. The patient receives up to 300 mg of LAF 237 daily when diarrhea occurs.

What is claimed is:

1. A combination which comprises (a) an antidiarrheal agent and (b) an epothilone derivative of formula I

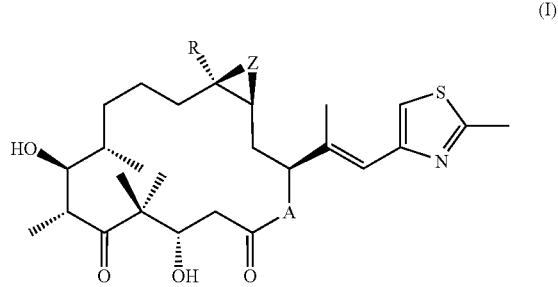

wherein A represents O or $NR_N$, wherein $R_N$ is hydrogen or lower alkyl, R is hydrogen or lower alkyl, and Z is O or a bond, in which the active ingredients (a) and (b) are present in each case in free form or in the form of a pharmaceutically acceptable salt and optionally at least one pharmaceutically acceptable carrier; for simultaneous, separate or sequential use.

2. Combination according to claim 1 comprising an epothilone derivative of formula I wherein A represents O, R is lower alkyl or hydrogen and Z is O or a bond.

3. A pharmaceutical composition comprising a quantity which is jointly therapeutically effective against a proliferative disease of a combination according to claim 1 and at least one pharmaceutically acceptable carrier.

4. A method for the treatment of a proliferative disease comprising administering a combination according to claim 1.

5. A method of preventing or controlling diarrhea associated with administering an epothilone derivative of formula I

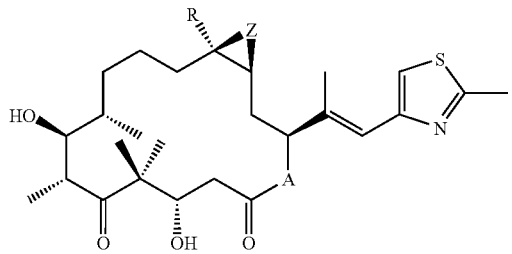
(I)

in which compound A represents O or $NR_N$, wherein $R_N$ is hydrogen or lower alkyl, R is hydrogen or lower alkyl, and Z is O or a bond, in free form or in the form of a pharmaceutically acceptable salt, to a patient, which comprises administering an effective amount of an antidiarrheal agent to the patient receiving treatment with the epothilone derivative.

6. The method of claim 5 wherein the epothilone derivative is epothilone B.

7. A method for the treatment of a proliferative disease comprising administering an antidiarrheal agent in combination with an epothilone derivative of formula I

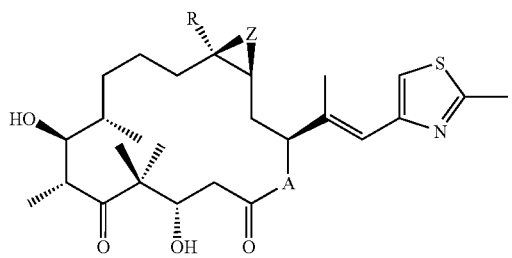
(I)

in which compound A represents O or $NR_N$, wherein $R_N$ is hydrogen or lower alkyl, R is hydrogen or lower alkyl, and Z is O or a bond.

8. A commercial package comprising (a) an antidiarrheal agent and (b) an epothilone derivative of formula I

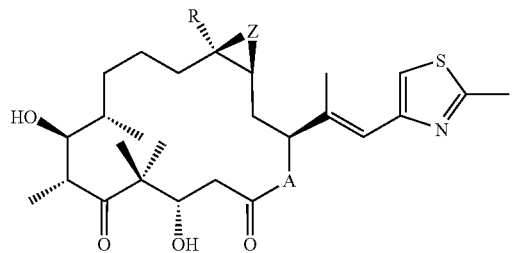
(I)

wherein A represents O or $NR_N$, wherein $R_N$ is hydrogen or lower alkyl, R is hydrogen or lower alkyl, and Z is O or a bond, together with instructions for simultaneous, separate or sequential use thereof in the treatment of a proliferative disease.

9. A combined preparation, which comprises (a) one or more unit dosage forms of an antidiarrheal agent and (b) one or more unit dosage forms of an epothilone derivative of formula I

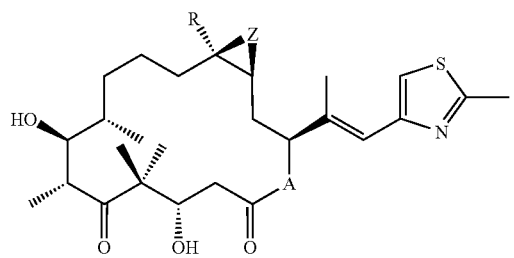
(I)

in which compound A represents O or $NR_N$, wherein $R_N$ is hydrogen or lower alkyl, R is hydrogen or lower alkyl, and Z is O or a bond, in free form or in the form of a pharmaceutically acceptable salt.

* * * * *